United States Patent
Lee et al.

(10) Patent No.: US 8,050,472 B2
(45) Date of Patent: Nov. 1, 2011

(54) METHOD OF ACQUIRING PHALANGE EDGE IMAGE AND SYSTEM THEREFOR

(75) Inventors: Soo-Yeul Lee, Daejeon (KR);
Jeong-Won Lee, Daejeon (KR);
Ji-Wook Jeong, Daejeon (KR);
Done-Sik Yoo, Daejeon (KR);
Seung-Hwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1035 days.

(21) Appl. No.: 11/933,048

(22) Filed: Oct. 31, 2007

(65) Prior Publication Data

US 2008/0139912 A1 Jun. 12, 2008

(30) Foreign Application Priority Data

Dec. 7, 2006 (KR) .................. 10-2006-0124129

(51) Int. Cl.
*G06K 9/00* (2006.01)

(52) U.S. Cl. ........ 382/128; 382/132; 382/129; 600/437; 600/438

(58) Field of Classification Search .............. 382/128, 382/132; 378/54; 600/437–438, 442, 443, 600/448, 449, 459; 73/549, 602

See application file for complete search history.

(56) References Cited

U.S. PATENT DOCUMENTS

| | | | | |
|---|---|---|---|---|
| 4,752,918 | A | * | 6/1988 | Boucher et al. ............... 367/158 |
| 5,696,805 | A | * | 12/1997 | Gaborski et al. ............... 378/54 |
| 6,246,745 | B1 | * | 6/2001 | Bi et al. ........................ 378/54 |
| 6,711,282 | B1 | * | 3/2004 | Liu et al. ....................... 382/132 |
| 7,678,049 | B2 | * | 3/2010 | Tsoref et al. .................. 600/437 |
| 2003/0065264 | A1 | | 4/2003 | Tsoref et al. |
| 2005/0196031 | A1 | * | 9/2005 | Hsieh et al. .................. 382/132 |

FOREIGN PATENT DOCUMENTS

| | | |
|---|---|---|
| KR | 1020050053488 A | 6/2005 |
| KR | 1020060008849 A | 1/2006 |
| KR | 20-0415744 | 5/2006 |
| KR | 1020060067880 A | 6/2006 |

* cited by examiner

*Primary Examiner* — Vikkram Bali
*Assistant Examiner* — Nancy Bitar (57) ABSTRACT

A method and system for acquiring a phalange edge image using an X-ray image of a hand are provided. The method includes: selecting a region of interest from an X-ray image of the hand; acquiring a soft tissue background gray level removed image by removing a soft tissue background gray level from the region of interest; and extracting a phalange edge image from the soft tissue background gray level removed image.

14 Claims, 6 Drawing Sheets

METHOD OF ACQUIRING PHALANGE EDGE IMAGE AND SYSTEM THEREFOR

CROSS-REFERENCE TO RELATED PATENT APPLICATION

This application claims the benefit of Korean Patent Application No. 10-2006-0124129, filed on Dec. 7, 2006, in the Korean Intellectual Property Office, the disclosure of which is incorporated herein in its entirety by reference.

BACKGROUND OF THE INVENTION

1. Field of the Invention

The present invention relates to a method of acquiring a phalange edge image and a system therefor, and more particularly, to a method of acquiring a phalange edge image extracted from an X-ray image of a hand, and a system therefor.

This work was supported by the IT R&D program of MIC/IITA [2005-S-069-02, Development of Wearable System Using Physiological Signal Processing]

2. Description of the Related Art

A technique for acquiring a phalange edge image extracted from an X-ray image is used to determine the bone age of a child.

As living standards improve, children's adult heights thereof generally increase. Short children, and their parents, worry that they will be short as adults. Therefore, child growth research has developed a technique for predicting the adult height of a child and a medical treatment for increasing adult height.

A child's adult height is predicted based on their bone age. Bone age is not a chronological age but a physiological age. The bone ages of persons who are completely grown are assumed to be equal. Therefore, bone age can be used to determine the remaining potential growth time of a child. If the bone age is larger than the chronological age, the remaining potential growth time is short, and the child has less opportunity to grow.

The bone age prediction method has been especially actively researched in Europe, where the Greulich-Pyle (GP) method based on atlas and the Tanner-Whitehouse (TW) method using a skeletal maturity score are widely used. The TW method is more objective than the GP method, and thus is most widely used. The TW method has been enhanced into the TW2 method, and in 2000, the TW3 method. If a child is predicted to have a short adult height, this can be increased through medical growth treatment. Methods of growth treatment include enhancing bone growth by injecting a growth hormone and prolonging the potential bone growth time.

In the TW3 method, radius, ulna, and short (RUS) bone scores and a carpal score are obtained by adding maturity scores of bone growth plates in the X-ray image of a hand. Generally, maturity stages of bone growth plate are divided into nine stages A to I, and each maturity stage is allocated a maturity score. A doctor determines the maturity stage of a bone using the TW3 method and calculates the maturity score thereof. Maturity scores of bones are added to calculate the RUS scores and the carpal score, giving the bone age of a child.

The results of determining the maturity stage differ among doctors, and even vary over time for the same doctor. Therefore, a more objective method of determining the bone maturity stage using a computer algorithm is required. Some bone maturity stage determination apparatuses using a computer algorithm have already been developed and used in clinics.

Most of the bone maturity stage determination apparatuses used in clinics are provided with only a tool for supporting a doctor to determine a TW3 bone age from an X-ray image, but not an automatic bone maturity determination unit. In addition, even in a bone maturity stage determination apparatus having a bone maturity determination function, a doctor needs to perform some operations. Even in a bone maturity stage determination apparatus having the automatic bone maturity determination unit, the result of the determination depends on the state of the X-ray imaging apparatus and the direction of the hand in the X-ray image, preventing the bone maturity from being determined accurately.

The bone maturity determination is performed by identifying and evaluating the change of shapes of epiphysis and metaphysis of the bone growth plate and a coupling state thereof. Since the shapes of the epiphysis and the metaphysis of the bone growth plate cannot be easily extracted from the X-ray image, it is difficult to implement the automatic bone maturity stage determination apparatus.

In general, in order to extract the shapes of the epiphysis and the metaphysis, a finger edge is detected, and after that, an edge detection mask is applied. Alternatively, a gray level threshold method may be used. When applying the edge detection mask to the epiphysis, the difference in the gray level between the epiphysis and the soft tissue background in the X-ray image is small, and thus the edge cannot be easily detected. On the other hand, when using the gray level threshold method, the threshold cannot be accurately set due to variations in the brightness of the neighboring soft tissue.

Therefore, a technique for accurately extracting the shapes of the epiphysis and the metaphysis from the X-ray image of a hand has been continuously researched. If the soft tissue background is removed from the X-ray image of the hand, the edges of the epiphysis and the metaphysis can be more easily extracted. Theoretically, using a dual-energy x-ray absorptiometry technique, an image of only the bone or soft tissue can be obtained. However, the image of only the bone or soft tissue cannot be accurately obtained by general X-ray absorption imaging techniques.

SUMMARY OF THE INVENTION

The present invention provides a method of acquiring an accurate phalange edge image, and a system therefor.

According to an aspect of the present invention, there is provided a method of acquiring a phalange edge image, comprising: selecting a region of interest from an X-ray image of a hand; acquiring a soft tissue background gray level removed image by removing a soft tissue background gray level from the region of interest; and extracting a phalange edge image from the soft tissue background gray level removed image.

According to another aspect of the present invention, there is provided a system for acquiring a phalange edge image, comprising: a gray level removed image acquiring unit which acquires an soft tissue background gray level removed image from a region of interest from an X-ray image of a hand; and a phalange edge image extracting unit which extracts a phalange edge image from the soft tissue background gray level removed image.

BRIEF DESCRIPTION OF THE DRAWINGS

The above and other aspects of the present invention will become more apparent by describing in detail exemplary embodiments thereof with reference to the attached drawings in which.

DETAILED DESCRIPTION OF THE PREFERRED EMBODIMENT

The present invention will now be described in detail by explaining exemplary embodiments of the invention with reference to the attached drawings. Like reference numerals denote like elements in the drawings.

Figure 1A:
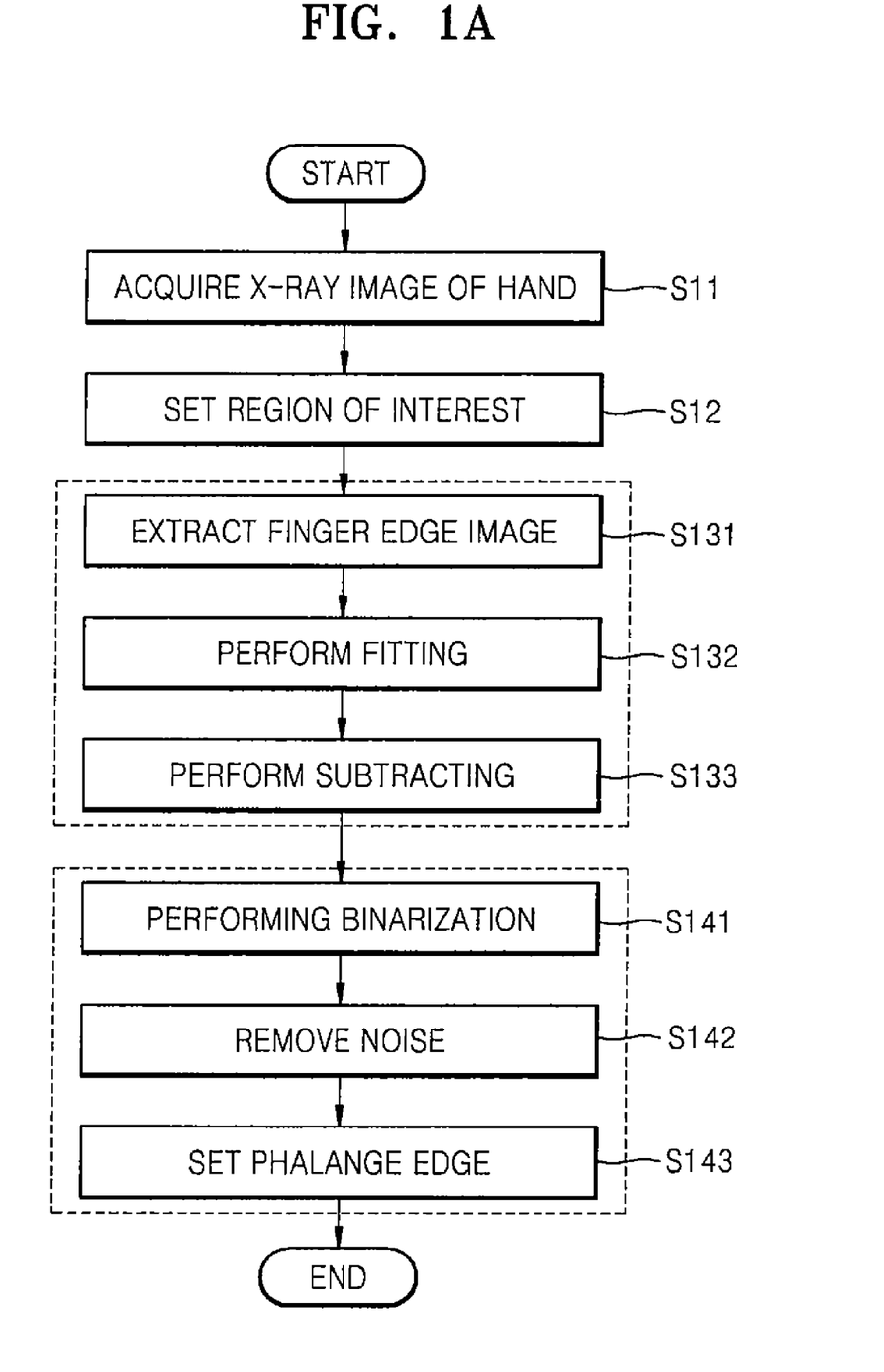
FIG. 1A is a flowchart of a method of acquiring a phalange edge image according to an embodiment of the present invention.
Figure 1B:
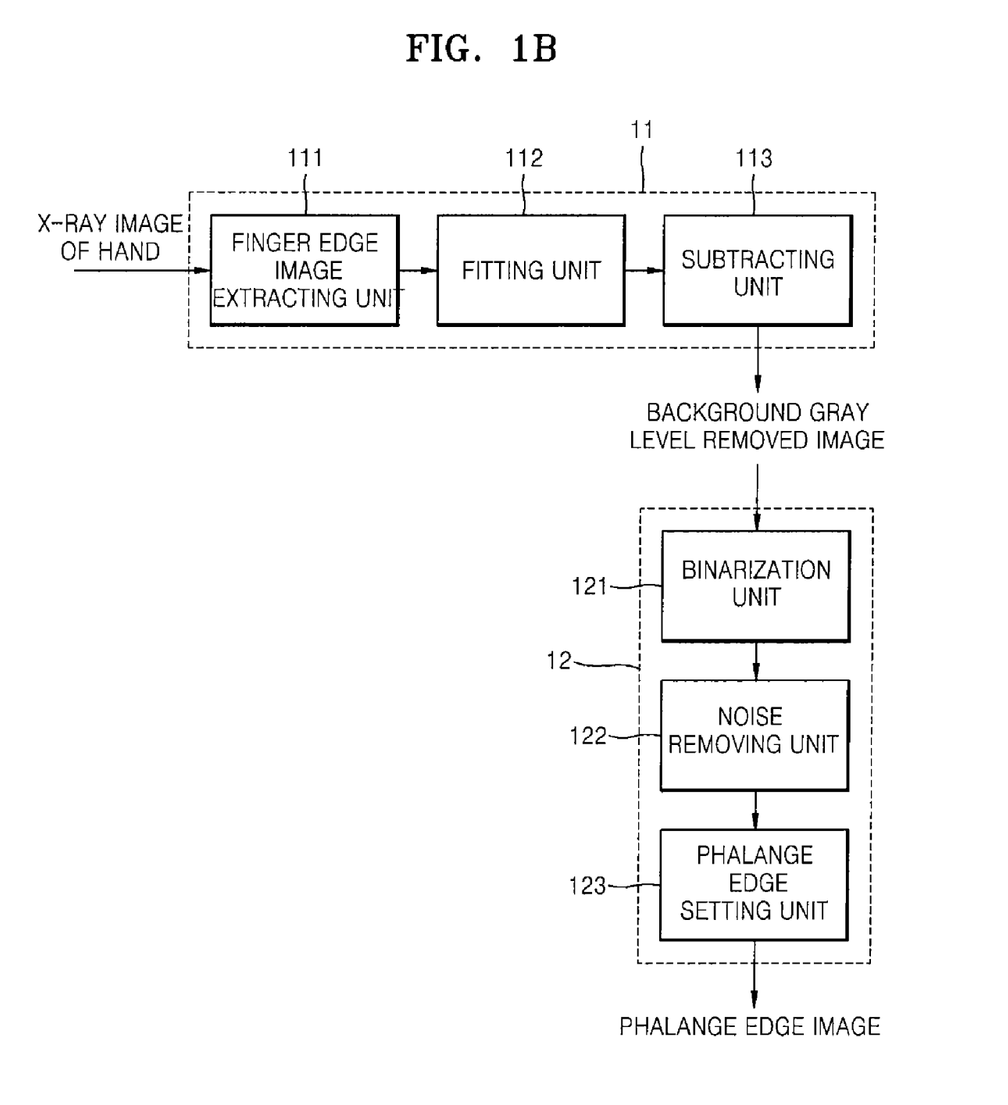
FIG. 1B shows a phalange edge acquiring system according to an embodiment of the present invention.

FIG. 1A is a flowchart of a method of acquiring a phalange edge image according to an embodiment of the present invention. FIG. 1B shows a phalange edge acquiring system according to an embodiment of the present invention.

Firstly, an X-ray image of a hand for extracting a phalange edge is acquired (S11). The X-ray image of the hand can be acquired by using film-based or digital X-ray imaging apparatus. In the embodiment, a soft tissue portion in the X-ray image of the hand needs to be processed. In addition, the brightness of an X-ray image of the hand is set so that both the soft tissue and the bone are distinguished. In addition, for measurement of the bone age, the hand in the X-ray image has all its fingers stretched and spread.

Figure 2:
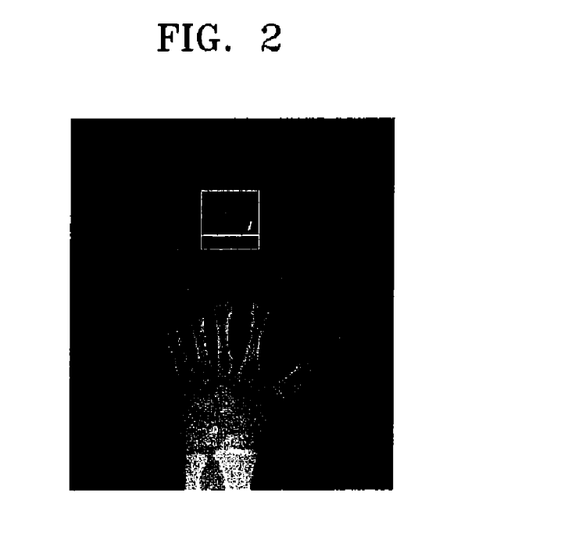
FIG. 2 is an X-ray image of a hand and a region of interest selected from the X-ray image of the hand.

FIG. 2 shows a region of interest selected to extract a phalange edge from an X-ray image of a hand.

A film-type X-ray imaging apparatus having a 45 kVp tube voltage and 3 mVs tube current is used. The X-ray film image is converted to a digital image by a film scanner. The spatial resolution of the digital image is 200 ppi (pixels per inch), and 256 (8 bit) gray levels are used.

In FIG. 2, the pixels of the X-ray image of the hand are represented by gray levels of X-ray intensities absorbed by the soft tissue and the bone. In an X-ray image of a child's hand, the gray levels of the bone (epiphysis and metaphysis) of the hand are not greatly distinguished from those of the soft tissue.

Therefore, the phalange edge cannot be easily extracted by applying a general edge detection mask to the X-ray image of child's hand. In addition, since the gray level of the soft tissue greatly changes across the X-ray image, the phalange edge cannot be easily extracted using threshold setting. Accordingly, the gray level of the soft tissue needs to be removed from the X-ray image of the hand, to substantially equalize the gray level of the background and allow the phalange edge to be easily extracted using the threshold setting.

After the X-ray image of the hand is acquired in operation S11, a region of interest for extracting the phalange edge is selected from the X-ray image of the hand (S12). The size of the region of interest is set so as to include left and right background of a finger. The center of the region is adjusted to a joint of the finger. An example of the region of interest is illustrated as a square of 200×200 pixels in FIG. 2.

After the region of interest is selected in operation S12, a gray level removed image acquiring unit 11 acquires a soft tissue background gray level removed image by removing soft tissue background gray level from the region of interest (S13).

To do so, a finger edge image is extracted from the region of interest (S131). Next, fitting of soft tissue gray level trends is performed (S132). An original gray level profile is subtracted according to the fitting (S133), so that the soft tissue background gray level is removed. Now, operations S131, S132, and S133 will be described in detail.

Figure 3A:
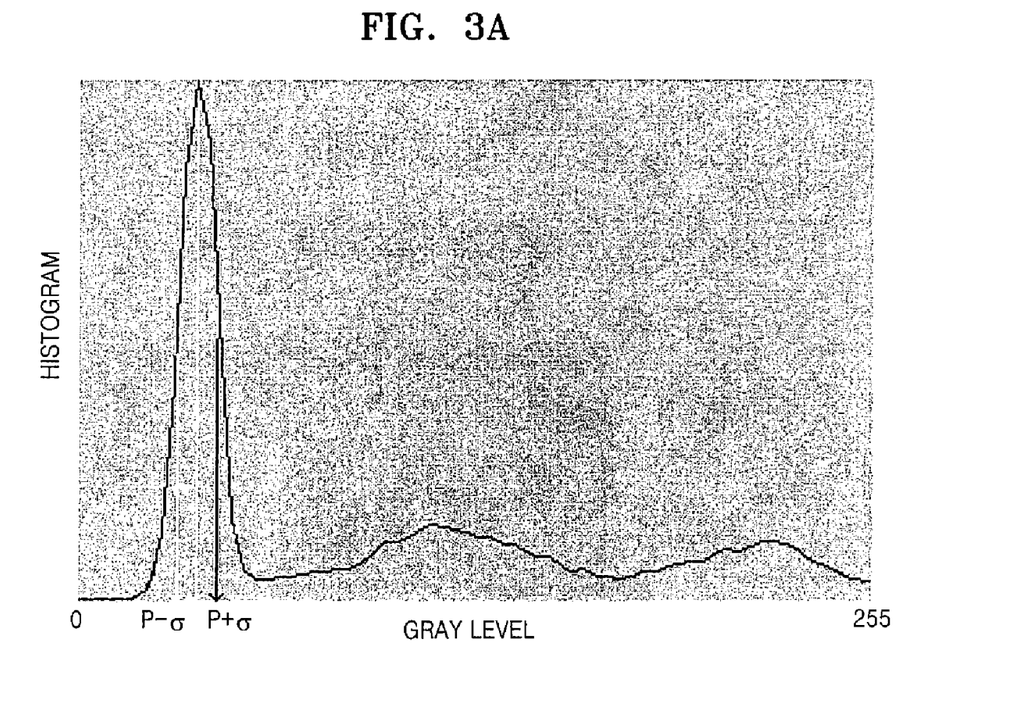
FIG. 3A is a histogram of gray levels of the region of interest of FIG. 2.

FIG. 3A is a histogram of gray levels of the region of interest.

In the histogram of FIG. 3A, a high peak in the dark region represents a gray level of the background. A low peak in the intermediate region represents a gray level of the soft tissue. A low peak in the bright region represents a gray level of the phalange including the epiphysis and the metaphysis. In some cases, the peak in the intermediate region may not be easily distinguished from that in the bright region.

Figure 3B:
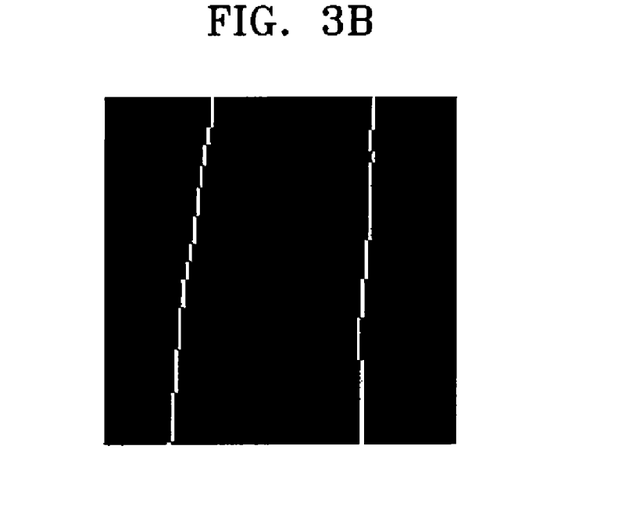
FIG. 3B is a finger edge image extracted from the region of interest of FIG. 2.

In order to acquire the finger edge image in operation S131, a finger edge image extracting unit 111 detects the gray level of the peak P in the dark region of the histogram (see P in FIG. 3A) and calculates the standard deviation σ of the peak P. The threshold may be set to a value of P to P+5σ to extract a binary image from the region of interest. In the embodiment, the threshold is set to P+σ. Pixels of the noise-removed binary image of which upper, lower, left, and right pixels have the gray level of 1 are designated as "0", other pixels are designated as "1", and the finger edge is determined based on the pixels designated as "1". An example of the finger edge image is illustrated in FIG. 3B.

After the finger edge image is extracted, a fitting unit 112 performs the fitting of the soft tissue gray level trend using a fitting function (S132). The fitting is a process for interpolating the soft tissue gray level trend into the phalange region.

Figure 3C:
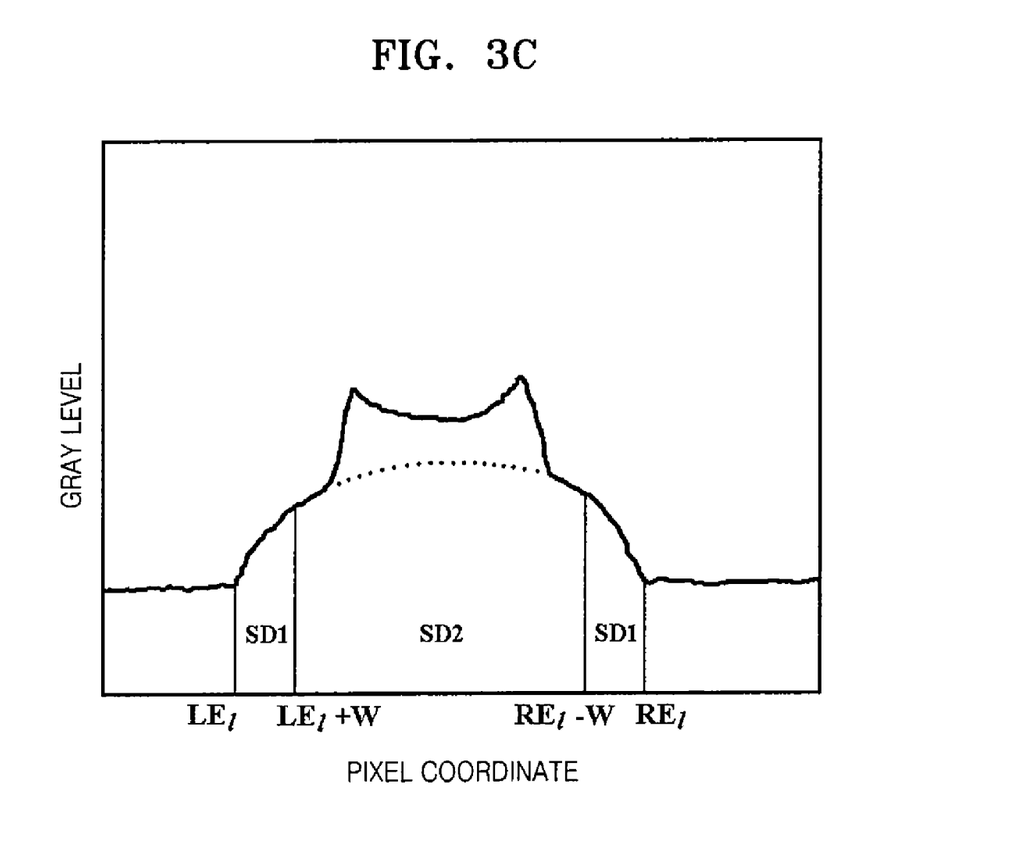
FIG. 3C is a gray level profile along a transversal line I across the region of interest of FIG. 2.

A transversal line I is set across the region of interest, and the gray level trend of the soft tissue along the transversal line I is fitted using the fitting function. The gray level profile of the region of interest along the transversal line I is schematically illustrated in FIG. 3C. Referring to FIG. 3C, in the gray level profile along the transversal line I, left and right soft tissue edges of the finger edge image extracted in operation S131 are denoted by LEI and REI.

The fitting needs to be performed on the gray level profile of the soft tissue between the LEI and the REI. However, since the soft tissue region cannot accurately determined in advance, the width W of the soft tissue needs to be considered. In a left soft tissue region between the LEI and the LEI+W and a right soft tissue region between the REI−W and the REI, the fitting is performed with first standard deviation SD1, that is, the standard deviation of the soft tissue. In a region between the LEI+W and the REI−W, the fitting is performed with a second standard deviation SD2, that is, the standard deviation of gray levels of portions excluding the soft tissue. In the embodiment, the second standard deviation SD2 is larger than the first standard deviation SD1, so that a higher weighting is allocated to the data of the soft tissue. In order to effectively obtain the advantage of the present invention, the second standard deviation may be two or more times larger than the first standard deviation SD1.

The fitting function may be a differentiable polynomial function. In the embodiment, a fourth order polynomial P(x)=

$C_0+C_1x+C_2x^2+C_3x^3+C_4x^4$ is used as the fitting function. In the polynomial function, $C_0$, $C_1$, $C_2$, $C_3$, and $C_4$ are fitting parameters, and x is a coordinate of a pixel. The fitting of the fitting function into the gray level between LEI to REI may be performed by using Levenberg-Marquardt fitting method. The result of the fitting is illustrated as a dotted line in FIG. 3C. The fitting is performed over the region of interest by shifting the transversal line I row by row.

Figure 3D:
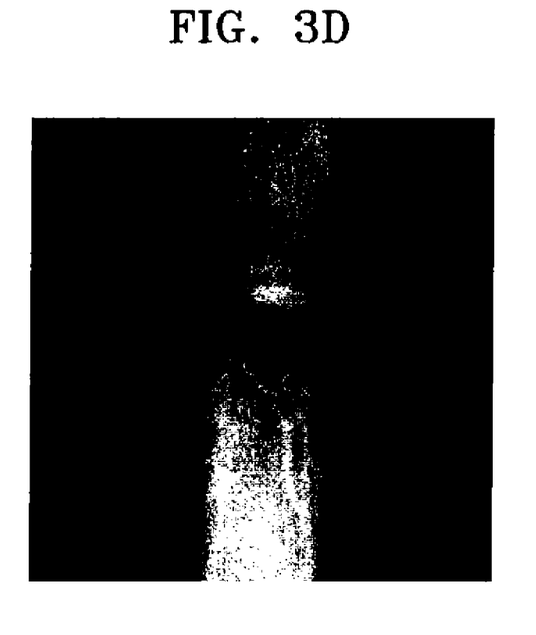
FIG. 3D is a soft tissue background gray level removed image where a soft tissue background gray level trend is removed from the region of interest of FIG. 2.

After the fitting, the subtracting unit 113 subtracts the gray level P(x) of the image obtained through the fitting from the gray level profile of the image obtained in operation S131 to obtain the soft tissue background gray level removed image (S133). An example of the soft tissue background gray level removed image in the region of interest is illustrated in FIG. 3D. The contrast of the soft tissue background gray level removed image is increased to improve visibility.

After the soft tissue background gray level is removed, an edge image extracting unit 12 extracts a phalange edge image from the soft tissue background gray level removed image (S14).

Referring to FIG. 3D, since the soft tissue background gray level trend is subtracted from the X-ray image of the region of interest, regions other than the phalange region are illustrated as a dark region having similar brightness. Therefore, the phalange region can be extracted by setting a suitable threshold. A binarization unit 121 sets the threshold according to the method used in operation S131 of extracting the finger edge image from the region of interest of which the soft tissue background gray level trend is subtracted. In this case, the histogram corresponds to the background gray level removed image.

Figure 4A:
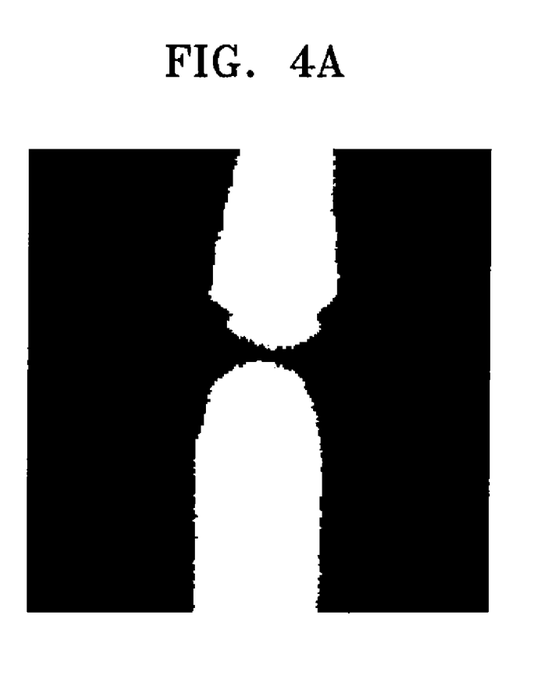
FIG. 4A is a phalange image obtained by binarizing the soft tissue background gray level removed image with a threshold and performing closing and opening.

The binarization unit 121 converts the background gray level removed image into a binary image based on the threshold (S141). A noise removing unit 122 performs an imaging process including closing and opening processes on the binary image to remove noise form the phalange and background regions (S142). The resulting noise-removed binary image is illustrated in FIG. 4A.

Figure 4B:
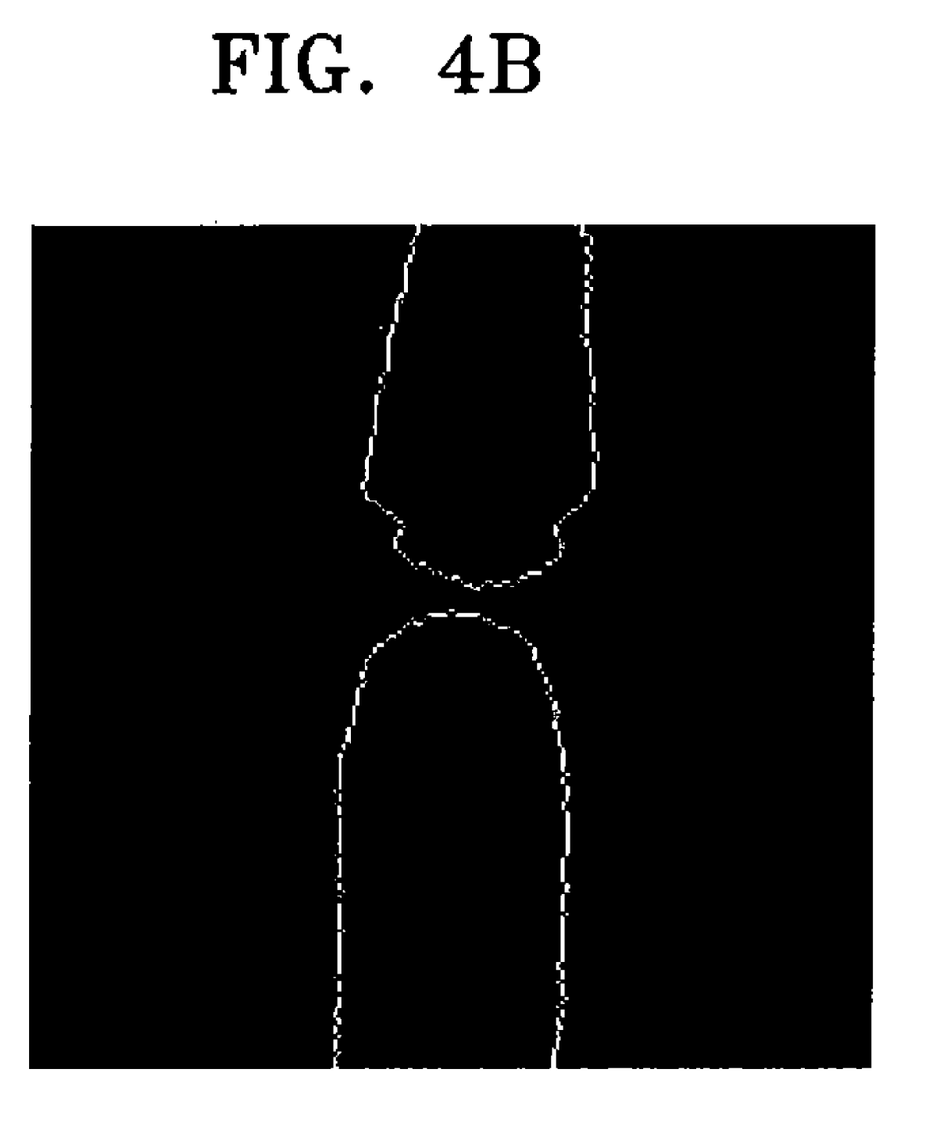
FIG. 4B is an example of a phalange edge image extracted from the image of FIG. 3A.

Next, a phalange edge determining unit 123 designates "0" to pixels of the noise-removed binary image of which upper, lower, left, and right pixels have the gray level of 1 and "1" to other pixels, and determines the phalange edge based on the pixels designated "1" (S143). In the binarization process, dark portions having a gray level of 0 may occur within the phalange region. These can cause an erroneous phalange edge to be extracted. In order to avoid the error, the phalange edge may be set as the leftmost and rightmost edges in the transversal line I across the region of interest. An example of the phalange edge image is illustrated in FIG. 4B.

According to the present invention, the accuracy of extraction of a phalange edge can be improved by using an X-ray image of a hand and removing a soft tissue background gray level trend from the X-ray image of the hand.

The invention can also be embodied as computer readable code on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion.

While the present invention has been particularly shown and described with reference to exemplary embodiments thereof, it will be understood by those skilled in the art that various changes in form and detail may be made therein without departing from the spirit and scope of the invention as defined by the appended claims. The exemplary embodiments should be considered in a descriptive sense only, and not for purposes of limitation. Therefore, the scope of the invention is defined not by the detailed description of the invention but by the appended claims, and all differences within the scope will be construed as being included in the present invention.

What is claimed is:

1. A method of acquiring a phalange edge image, comprising:
   (a) selecting a region of interest from an X-ray image of a hand;
   (b) acquiring a soft tissue background gray level removed image by removing a soft tissue background gray level from the region of interest; and
   (c) extracting a phalange edge image from the soft tissue background gray level removed image,
   wherein the step (b) of removing the soft tissue background gray level comprises:
      (b1) extracting a finger edge image from the region of interest, the finger edge image including a soft tissue region and a phalange region;
      (b2) performing fitting to interpolate a gray level of the soft tissue region in the finger edge image into the phalange region; and
      (b3) subtracting a gray level of an image obtained by the fitting from a gray level of the finger edge image in order to acquire the soft tissue background gray level removed image.

2. The method of claim 1, wherein the step (c) of extracting the phalange edge image comprises:
   (c1) obtaining a binary image of the soft tissue background gray level removed image by applying a first threshold to the soft tissue background gray level removed image; and
   (c2) designating "0" to pixels of the binary image, of which upper, lower, left, and right pixels have the gray level of "1", and "1" to remaining pixels, and determining the phalange edge based on the pixels designated "1".

3. The method of claim 1,
   wherein the step (b1) of extracting the finger edge image is performed by setting a second threshold to a value in the range of P to P+5σ, and
   wherein P is a gray level of a first peak in a dark region of a histogram of the region of interest, and σ is a standard deviation of the first peak.

4. The method of claim 1,
   wherein the step (b2) of performing fitting is performed using a fitting function, and
   wherein the fitting function is a differentiable polynomial function.

5. The method of claim 1, wherein the step (b2) of performing fitting is performed using Levenberg-Marquardt fitting method.

6. The method of claim 1,
   wherein the step (b2) of performing fitting is performed on pixels at a predetermined distance from the finger edge by using a first standard deviation SD1 and on other pixels by using a second standard deviation SD2, and
   wherein the second standard deviation SD2 is larger than the first standard deviation SD1.

7. The method of claim 2,
wherein the first threshold in the step (c1) of obtaining the binary image is set to a value in the range of P to P+5σ, and
wherein P is a gray level of a first peak in a dark region of a histogram of the soft tissue background gray level removed image, and σ is a standard deviation of the first peak.

8. A system for acquiring a phalange edge image, comprising:
a gray level removed image acquiring unit configured to acquire a soft tissue background gray level removed image from a region of interest from an X-ray image of a hand; and
a phalange edge image extracting unit configured to extract a phalange edge image from the soft tissue background gray level removed image,
wherein the gray level removed image acquiring unit comprises:
a finger edge image extracting unit configured to extract the finger edge image from the region of interest;
a fitting unit configured to perform fitting to interpolate the gray level of the soft tissue in the finger image into the phalange region; and
a subtracting unit configured to subtract the gray level of the image obtained by the fitting from the gray level of the finger image.

9. The system of claim 8, wherein the phalange edge image extracting unit comprises:
a binarization unit configured to obtain a binary image of the soft tissue background gray level removed image by applying a first threshold to the soft tissue background gray level removed image; and
a phalange edge determining unit configured to designate "0" to pixels of the binary image, of which upper, lower, left, and right pixels have the gray level of "1", and "1" to remaining pixels, and determine the phalange edge based on the pixels designated "1".

10. The system of claim 8,
wherein the finger edge image extracting unit is configured to set a second threshold for extracting the finger edge image,
wherein the second threshold is set to a value in the range of P to P+5σ, and
wherein P is a gray level of a first peak in a dark region of a histogram of the region of interest, and σ is a standard deviation of the first peak.

11. The system of claim 8,
wherein the first and the second fitting units perform the fittings using a first fitting function and a second fitting function, and
wherein the first and the second fitting functions are each a differentiable polynomial function.

12. The system of claim 8, wherein the fitting is performed using Levenberg-Marquardt fitting method.

13. The system of claim 8,
wherein the fitting unit performs the fitting on pixels at a predetermined distance from the finger edge by using a first standard deviation SD1 and on other pixels by using a second standard deviation SD2, and
wherein the second standard deviation SD2 is larger than the first standard deviation SD1.

14. The system of claim 9, wherein the binarization unit sets the first threshold to a value in the range of P to P+5σ, and
wherein P is a gray level of a first peak in a dark region of a histogram of the soft tissue background gray level removed image, and a is a standard deviation of the first peak.

* * * * *